United States Patent [19]

Bull

[11] 4,039,807
[45] Aug. 2, 1977

[54] ELECTRON BEAM DEFLECTION ARRANGEMENTS HAVING PRESHAPING OF THE BEAM

[75] Inventor: Eric William Bull, Sunbury-on-Thames, England

[73] Assignee: EMI Limited, Middlesex, England

[21] Appl. No.: 703,238

[22] Filed: July 7, 1976

[30] Foreign Application Priority Data

July 11, 1975  United Kingdom ............... 29182/75

[51] Int. Cl.² ..................... A61B 6/02; G03B 41/16
[52] U.S. Cl. ................................. 250/360; 250/403; 250/416 TV; 250/445 T
[58] Field of Search ........... 250/360, 366, 369, 445 T, 250/416 TV, 403

[56] References Cited

U.S. PATENT DOCUMENTS

4,002,917  1/1977  Mayo ............................... 250/445 T
4,010,370  3/1977  Lemay ............................. 250/445 T

*Primary Examiner*—Alfred E. Smith
*Assistant Examiner*—T. N. Grigsby
*Attorney, Agent, or Firm*—Cooper, Dunham, Clark, Griffin & Moran

[57] ABSTRACT

In an X-ray source for radiographic apparatus of the type known as computerized axial tomography (CAT) scanners it has been suggested to scan a beam of electrons across a target/anode to correspondingly scan a beam of X-rays relative to a patient. The target is inclined to the electrons mean direction to direct the X-rays in another direction. If a ribbon shaped beam of electrons is used then the shape and orientation of the region of contact, of the electrons, changes. It is proposed to preshape and preorientate the electron beam to retain the desired region of contact, and hence the desired X-ray distribution, during the scanning.

12 Claims, 8 Drawing Figures

ELECTRON BEAM DEFLECTION ARRANGEMENTS HAVING PRESHAPING OF THE BEAM

The present invention relates to the deflection of ribbon-like electron beams in X-ray tubes and is particularly related to the deflection of such beams of electrons in X-ray tubes used, for example, in scanning radiographic apparatus.

In scanning radiographic apparatus, such as that described U.S. Pat. No. 3,946,234 in which one or more beams of radiation are scanned across a section of a body, it can be convenient to provide a non-mechanical scan of the X-ray beam. Such a scan can be achieved by scanning an incident beam, typically ribbon-like, of electrons across an extended anode target 50 as to vary the point of incidence and, therefore, the position of the emitted X-rays. A typical apparatus using such a scanning X-ray tube is shown in U.S. application Ser. No. 630,779 now U.S. Pat. No. 4,101,370.

In the course of such scanning the beam of electrons, which is arranged to be a flat, ribbon-like strip when undeflected, may be distorted as a result of the scanning fields to give consequent distortion of the X-ray beam. Distortion of the X-ray beam may also occur as a result of an oblique angle of incidence, of the ribbon beam of electrons, on the anode. It is however desirable to maintain the incidence, of the electron beam on the target, at the same orientation during scanning, to maintain a desired X-ray distribution.

Scanning of electron beams is well known from, for example, television or electron beam welding technology. Such scanning can provide distortion of the electron beams, usually circularly symmetrical, used. Techniques have been disclosed for using circularly symmetrical coil arrangements to correct such distortion, typically by introducing an opposing distortion. A typical arrangement is disclosed in British Pat. No. 1,078,826 which relates to electron beam welding. In the specification of that Patent, there is shown a circularly symmetrical arrangement of six coils used to pre-distort an electron beam to maintain a circular cross-section for the beam during scanning over a workpiece.

British Pat. No. 1,078,826 and similar publications do not, however, provide any teaching on the desirability of maintaining the orientation of the region of incidence of a scanned ribbon-like electron beam on an inclined X-ray target. Neither do they provide any teaching as to a suitable means for achieving this. It is an object of this invention to provide a means for maintaining the correct orientation of this region of incidence in such X-ray tubes.

According to the invention there is provided an X-ray tube including a source of a ribbon-like beam of electrons, being relatively narrow in a first direction perpendicular to the direction of travel of the beam and relatively wide in a second direction orthogonal to the first direction and direction of travel, a target extended in the first direction and having a surface inclined to the second direction to project X-rays substantially about in a chosen direction, which may be the second direction, in response to electrons incident thereon, means for deflecting the beam of electrons to scan the region of incidence of the beam along the target in the first direction and correction means for changing the shape of the beam of electrons in dependence on the said deflection so that the region of incidence of the deflected beam remains a linear region substantially parallel to the region of incidence of the undeflected beam.

In one embodiment of the invention the said correction means is arranged to correct for curvature of the said region of incidence, dependent on the extent of the deflection, by introducing a precurvature, of the electron beam, dependent in the opposite sense on the deflection.

In another embodiment of the invention the said correction means is arranged to incline the said beam of electrons, to the undeflected beam, through an angle proportional to the said deflection to maintain the region of incidence of the deflected beam substantially parallel to that of the undeflected beam despite the inclined disposition of the surface of said target.

Preferably the said correction means provides both an inclination of the electron beam and a precurvature.

In order that the ivention may be clearly understood and readily carried into effect examples thereof will now be described with reference to the accompanying drawings of which.

Figure 1:
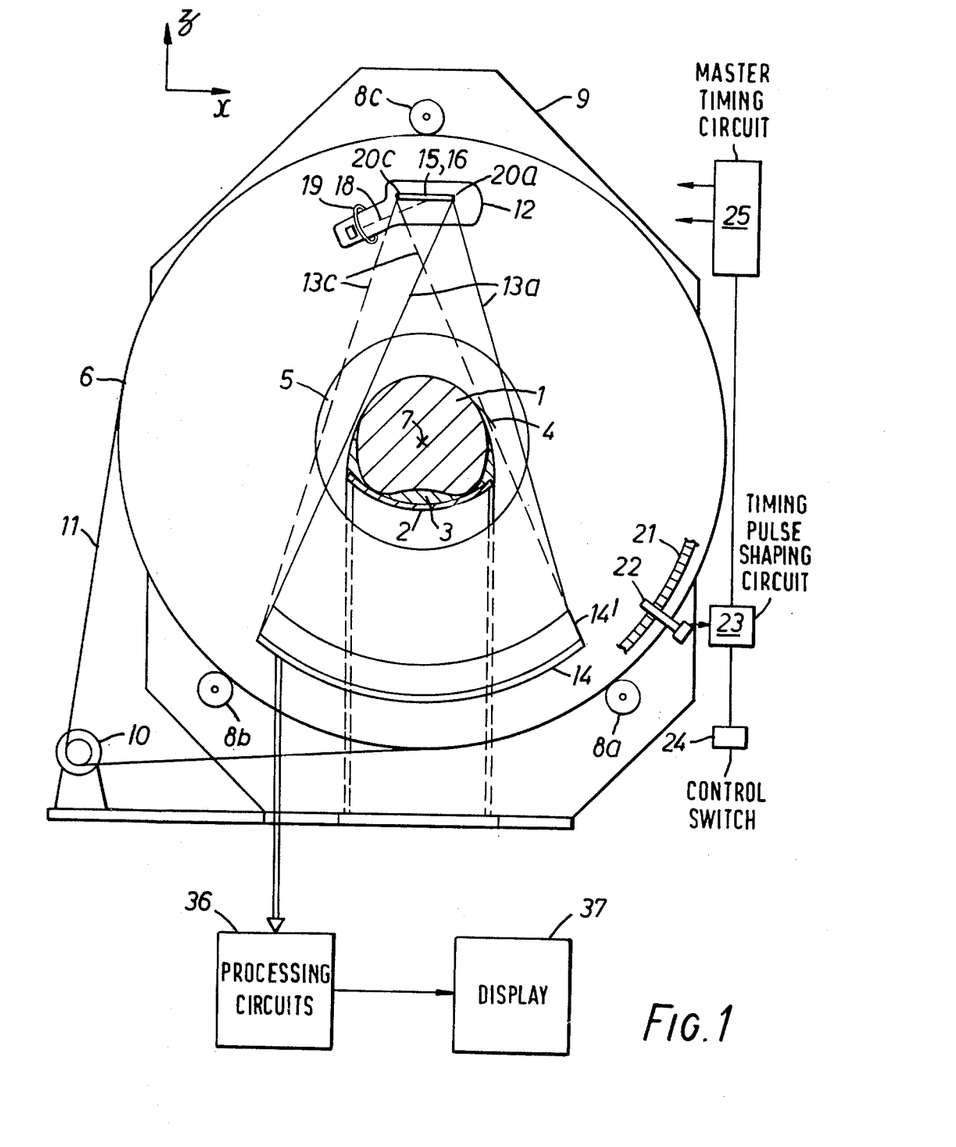
FIG. 1 shows a typical apparatus using a X-ray tube of the type incorporating the invention.

There is shown in FIG. 1 a typical example of a radiographic apparatus, of the type known as computerised axial tomography (CAT) scanners, in a development which includes a scanning X-ray tube.

A body, 1, of a patient to be examined, shown in transverse section, is supported on a suitably shaped bed 2, also shown in transverse section. A material 3, having an absorption, to the X-radiation, similar to that of body tissue, is positioned between the body 1 and the bed 2, to substantially exclude air from gaps therebetween.

Material 3 is also extended partly about the body to provide an approximately circular cross-section to the radiation. The body is retained firmly in the desired position by means such as a restraining strap 4.

The bed 2 and the body 1 are inserted into an aperture 5 in a rotatable member 6 so that a desired part of the body is centred in the aperture. The rotatable member 6 is arranged to rotate about an axis 7, generally longitudinal of the body 1, which is shown perpendicular to the paper. For that purpose it is supported by three gear wheels 8 a,b,c which engage with gear teeth, not shown, cut into the periphery of member 6. The gear wheels 8 are journalled in a main frame 9 of the apparatus. Member 6 is driven by an electric motor 10 via a toothed belt 11 which runs around and engages with the periphery of member 6 in a position displaced from gear wheels 8 in a direction perpendicular to the plane of the drawing.

The rotatable member 6 also carries a source 12 of x-rays 13, a bank of detectors 14 and associated collimators 14'.

The source 12 includes an elongated target/anode structure 15, 16, an electron gun 17, which produces a beam of electrons 18 and deflection coils, illustrated generally at 19 by a toroidal former although saddle-shaped coils or deflection plates, for example, could be used if desired. Two extreme source point positions 20a and 20c, producing fans of X-rays 13a and 13c, are shown from which it can be seen that, at any position of the source spot, the fan of X-rays 13 encompasses the body and is incident on the detectors 14. It will be appreciated that the detectors should be capable of receiving radiation for any position of the source spot 20 and that the collimator 15 should be suitable to allow this.

In operation the detectors, which in a typical example number 200, receive radiation from the source spot 20. Motor 10 provides a continuous rotation of member 6 and the equipment mounted thereon and the outputs of the detectors are integrated over suitable periods to provide output signals related to radiation traversing the body along discrete beam paths. The spot 20 is also traversed along target/anode 15, 16 in a predetermined relationship with the rotary motion to provide the beam paths at a desired orientation in the body. The output signals can then be processed, (in processing circuits generally indicated at 36) for example as described in U.S. Pat. No. 3,924,129 to provide a distribution of the distribution of the absorption of the radiation in a region of the body for display on display unit 37.

A suitable relationship between source spot scan and rotation is described in U.S. application Ser. B No. 630,779 now U.S. Pat. No. 4,010,370.

Rotary member 6 also carries a graticule 21 which is a transparent substrate carrying engraved lines. A photocell and light source unit 22 provides signals caused by interruptions of a light path by the engraved lines and hence indicative of the rotation. These signals are used to operate integrators, included in processing circuit 36 for integrating the output signals. They are also applied to a timing pulse shaping circuit 23, which also receives start and stop signals from a control switch 24. The shaped pulses from circuit 32 are fed to a master timing circuit 25 which is arranged to generate deflection waveforms for application to the coils 19 of tube 12 to relate the source spot scan with the rotation.

It will be understood that any other suitable method of deriving timing signals, and using them to control the source spot scan, may be used if desired. It should also be noted that the orientation of the components of tube 12 has been shown as in FIG. 1 for the sake of clarity although the orientations to be shown hereinafter represent a more practical arrangement.

Figure 2:
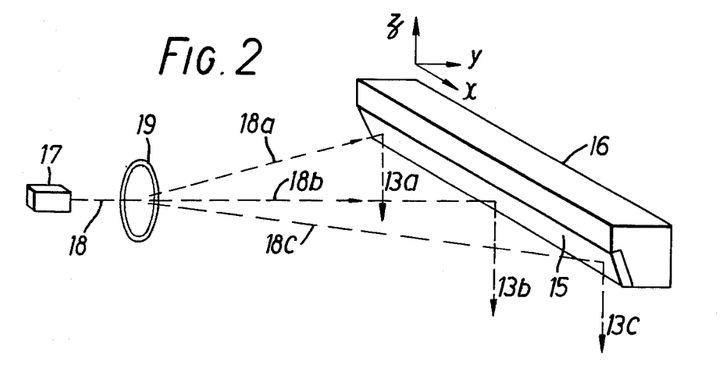
FIGS. 2 and 3a and 3b are diagrams used to explain the basic operation of such X-ray tubes.

Turning now to the tube 12 in more detail, this is shown in FIG. 2 in a still simplified form in which components, such as the tube envelope and cooling connections, not necessary to an understanding of the invention have been omitted. To aid in explanation of the invention orthogonal axes in x, y and z directions have been indicated.

The beam 18 of electrons is suitably focussed and arranged to strike the target 15 over an area of small dimension in the x direction of the coordinates shown. Target 15, which may be made of tungsten, is insert into the anode member 16 which is at a suitable positive potential relative to the gun 17. Anode member 16 may be made of copper and is cooled appropriately. The anode member and the target may be of a cross section similar to those of any suitable known X-ray source. However in the present invention they are of extended length in the x direction. Electron beam scanning means 19, indicated as in FIG. 1 by a schematic toroidal former are provided to scan electron beam along target 15 in the x-direction to cause it to take up successive positions there-along, some of which are shown at 18a 18b and 18c. X rays 13 are emitted from the target, at the points at which the electron beam strikes it, predominantly at an angle of about 5° to the electron beam, for X-rays produced by electrons of energy in the region of 10 kilo electron volts. Means, which will be further discussed hereinafter, are provided to restrict the X-rays, emitted from the source, substantially to the required direction, indicated by arrows 13, and those X-rays are allowed to leave the tube by means of a suitable window.

The linear scanning motion, required as described hereinbefore is provided by arranging for the deflection means 19 to scan electron beam 18 along target 15 as appropriate. The source and detector array are, as previously described, rotated about a common axis, shown in FIG. 1 in the y-direction.

Figure 3A:
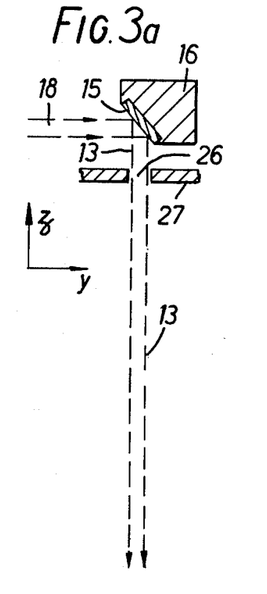
Figure 3B:
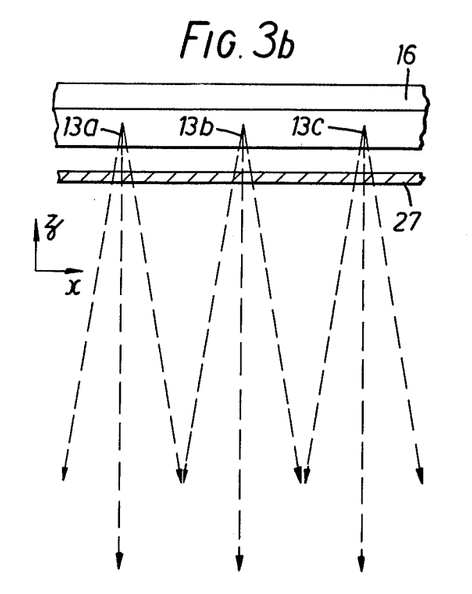

A suitable collimating arrangement, for restricting the emitted X-rays to the desired region, is indicated in FIG. 3 which is related to FIG. 2 as shown by the co-ordinates x, y and z. The scanning of te X-ray beam in the x direction is indicated by 13a, 13b and 13c corresponding to 18a 18b 18c. The X-ray beam is restricted by a slit 26 in an absorbing shield 27 so that it does not irradiate in the y direction a region greater than the required thickness of the region of body 1 to be examined. Absorbing shield 27 may be provided in the wall of the X-ray tube if desired or may be internal or external to the tube. Slit 26 is of a length chosen to allow the desired range of scan. It will be appreciated that this collimating arrangement allows some spreading of the beams in the x direction, as indicated in the Figure. To the extent that this spreading is greater than that required, to irradiate the fully array of dectectors, further collimators, not shown, may be provided to restrict such spread. Furthermore, errors due to the angular distribution of energy in the fan beam of the X-ray system can be compensated in the computation of the map of absorption coefficients. For that purpose the system is first calibrated, i.e. the X-ray distribution is measured with known absorption between source and detectors.

The shape of the anode member 16 and target 15 may be chosen to suit any required application of a scanning X-ray source.

The arrangement described thus far is similar in all essential respects to those described in U.S. Application No. 608,276 now Patent No. 4,002,917 and U.S. application No. 630,779. now U.S. Pat. No. 4,010,370. In a typical embodiment the electron beam 18 is ribbon shaped to be incident on the target 15 along a line perpendicular to the x-direction to produce an X-ray beam of a desired thickness in the y-direction as shown in FIG. 3a. It is required for that all positions of the scan of the source of X-rays on target 15, the line of incidence of the electrons thereon should remain perpendicular to the x-direction, to prevent undesirable distortion of the X-ray beam. However two factors tend to disturb this line of incidence. Both of these factors may be corrected by modifications to the electron beam scanning arrangements to change the form of the beam as will be described hereinafter. However these two factors are actually different effects and will be described individually.

The ribbon-like beam of electrons is in the form of a thin strip of large dimension in one direction perpendicular to the direction of travel of the electrons and relatively narrow in the orthogonal direction. The direction of the large dimension, which may be called the width of the ribbon, is in this example that given as the z direction in the earlier figures and the narrow dimension, called the thickness, and the direction of propagation being orthogonal and thus the x and y directions respectively.

Figure 4:
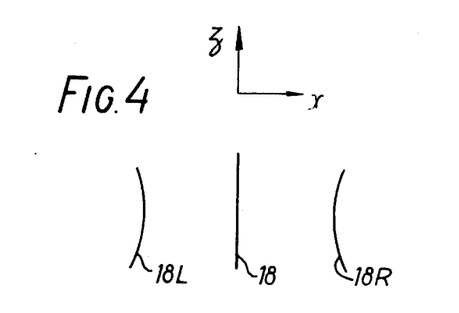
FIG. 4 is a diagram used to explain a form of distortion of the electron beam.

FIG. 4 shows at 18 the undeflected beam with the direction of propagation, the y axis, being into the paper and the x, z axes being as shown. For the purposes of scanning, the beam is to be deflected to the right or left in the x direction and should remain parallel to the z-axis. However on deflection by a typical known deflection coil of cosinusoidal current distribution, the beam shape becomes distorted as shown for the left and right deflected beams at 18L and 18R. A corresponding distortion is then produced on the line of incidence, of beams 18L and 18R, on target 15. The beam width is decreased by an amount dependent on that width and the square of the angle of deflection and it is curved by an amount proportional to the angle of deflection and the square of the beam width.

The change in the electron beam width can be corrected by known means which, however, do not correct the curvature and one aspect of the present invention is intended to provide the latter correction. It should be noted that the present invention may also provide correction for the change in the beam width.

Figure 5:
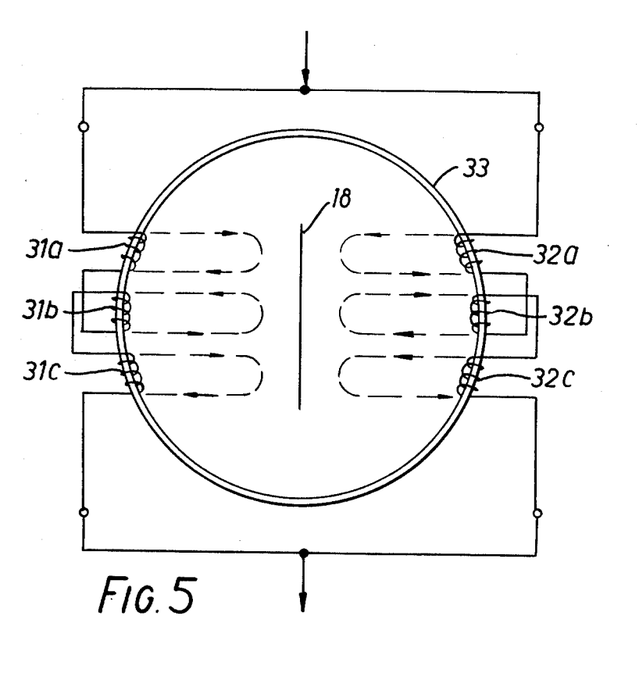
FIG. 5 shows a coil arrangement used to correct for this distortion.

The arrangement for this aspect of the invention is shown in FIG. 5. Windings 31a, b, c and 32a, b, c are provided on a toroidal magnetic core 33. This may be the same core as that used for the main scanning coils or may be provided separately. The windings are arranged to occupy substantially the same length of the core as the dimension of the beam width. The outer section 31a, c and 32a, c are each T turns wound in the same direction and deflect the outer parts of the beam in one direction while the centre sections 31b and 32b, each 2T turns wound in opposition, deflect the centre of the beam in the opposite direction. The fields produced are shown by the broken lines and it will be seen that such an arrangement tends to correct for the curvature indicated in FIG. 4. The current passed through the coils is of the same waveform as the main scanning current and of a suitable amplitude for proper correction.

Figure 6:
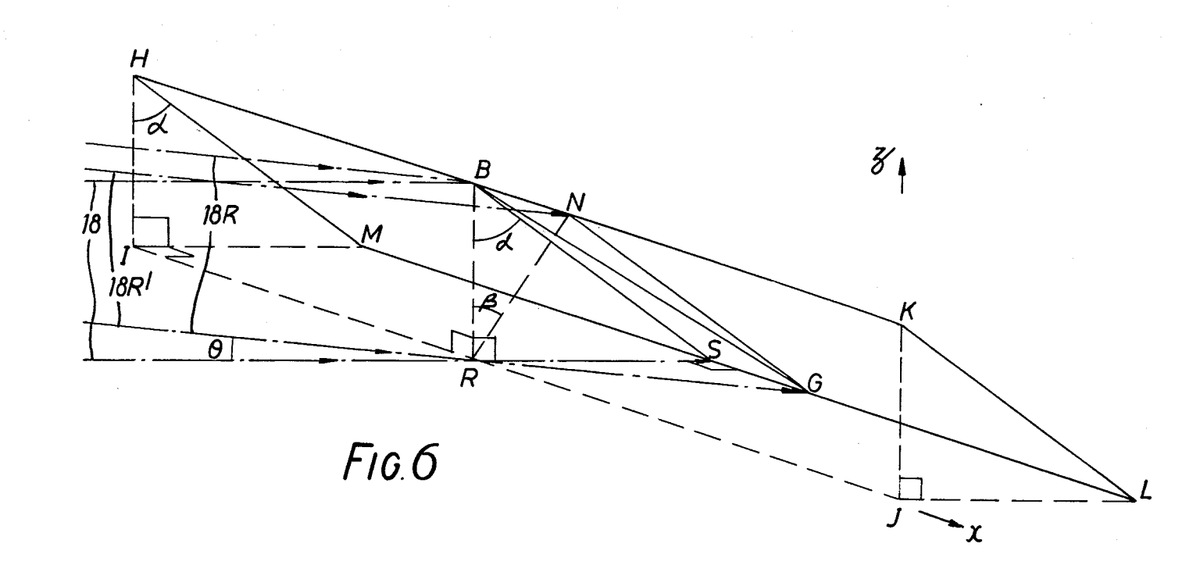
FIG. 6 is a diagram illustrating the effect, on the region of incidence on the target, of deflection of the electron beam

The second form of distortion of the x-ray beam results from the disposition of the X-ray target used, and the incidence of the deflected electron beam thereon. The arrangement is shown in FIG. 6 in a perspective view. In that Figure the surface HMLK shown by solid lines represents part of the surface of target 15 on which electrons are incident from the right. Possible positions of the electron beam are shown by the arrowed lines and certain broken lines have been shown to aid in understanding of the geometry of the arrangement. Certain right angles have been indicated for the same purpose. The target HMLK is inclined at an angle $\alpha$ to the $x\, z$ plane HIJK in order to project the emitted X-rays in a desired downwards direction. Undeflected beam 18 intersects plane HIJK at BR and is incident on the target at line BS in a $z\, y$ plane and inclined at angle $\alpha$ to the $z$ axis. A deflected beam will, of course, be emitted by the same source and will intersect plane HIJK at a different point. From the point of view of the geometry, however, it is convenient to consider that a deflection of angle $\theta$ has been obtained by moving the source so that a deflected beam 18R intersects plane HIJK on the same line BR, the deflection being only in an $x\, y$ plane. In that case it will be apparent that deflected beam 18R strikes the target on the line BG and that, because of the inclination of the target, line BG is inclined in the $x$ direction. This produces the undesirable distortion of the x-ray beam which it is desired to correct, the ideal situation being that the line of incidence of a beam on the target is always in a $y\, z$ plane.

It will be apparent that the desired effect will be achieved from a beam deflection angle $\theta$ if the beam is incident on line NG parallel to line BS. It will also be apparent that a deflected beam 18R', for which that is true, intersects plane HIJK at line NR inclined at angle $\beta$ to BR. In fact the correction is achieved by tilting the deflected beam at an angle $\beta$ to the $z$ direction.

Analysing the geometry of the situation it will be seen that $$\tan \theta = SG/RS$$

and $$\tan \alpha = RS/BR$$

so that $$\tan \theta \tan \alpha = SG/BR$$

Also $$\tan \beta = BN/BR \text{ and since } BN = SG$$
$$\tan \beta = \tan \theta \tan \alpha \qquad (1)$$

The apparatus of the invention is therefore arranged to rotate the deflected beam through an angle $\beta$ defined by equation (1) in terms of the deflection angle $\theta$ and the target tilt angle $\alpha$.

Figure 7:
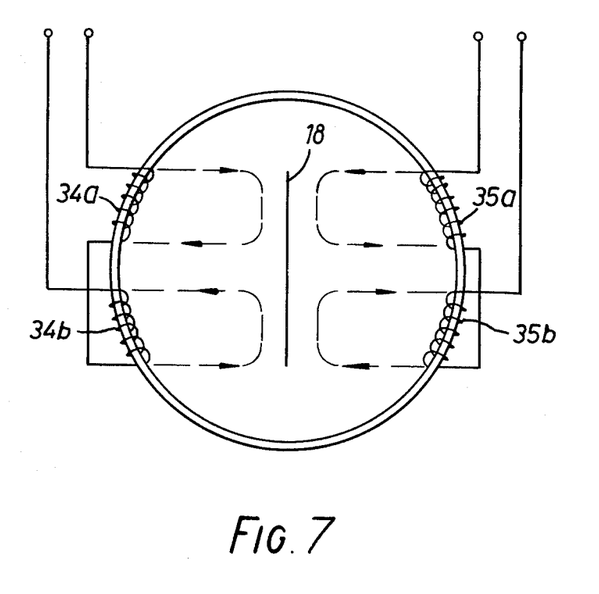
FIG. 7 shows a coil arrangement used to correct for this effect.

The arrangement, shown in FIG. 7 shows four coils 34a, b and 35a, b wound around a toroidal core 36 which is similar to core 33 of FIG. 5. Each half a and b of a pair of coils has an equal number of turns, the two halves being connected in opposition to give the field pattern shown by the broken lines. A scanning current proportional to tan $\theta$, tan $\alpha$ being constant, is fed to the coils at a suitable amplitude to keep the beam vertical for all scanning positions.

It will be understood that the toroidal cores shown for both of these examples can precede, or be included in, the windings of the main scanning coil, as desired. Square yokes or saddle type coils can also be employed instead of a toroid to achieve similar results or electrostatic deflection arrangements to give the same result can be devised.

What I claim is:

1. An X-ray tube including a source of a ribbon-like beam of electrons, being relatively narrow in a first direction perpendicular to the direction of travel of the beam and relatively wide in a second direction orthogonal to the first direction and direction of travel, a target extended in the first direction and having a surface inclined to the second direction to project x-rays substantially about a chosen direction, which may be the second direction, in response to electrons incident thereon, means for deflecting the beam of electrons to scan the region of incidence of the beam along the target in the first direction and correction means for changing the shape of the beam of electrons in dependence on said deflection so that the region of incidence of the deflected beams remains a linear region substantially parallel to the region of incidence of the undeflected beam.

2. An X-ray tube according to claim 1 wherein the said correction means is arranged to correct for curvature of the said region of incidence, related to the extent of the deflection, by introducing a precurvature, of the electron beam, dependent on the deflection in the opposite sense.

3. An X-ray tube according to claim 2 wherein the said correction means is arranged to additionally deflect the centre of said beam in one directon and the extreme regions in the opposite direction to provide the said opposite curvature.

4. An X-ray tube according to claim 3 wherein the said correction means includes a plurality of coils on each side of the said beam in the first direction.

5. An X-ray tube according to claim 4 wherein the said correction means comprises six coils arranged so that adjacent coils produce magnetic fields of opposite polarity.

6. An X-ray tube according to claim 4 wherein the said coils are included in a coil system also arranged to form said deflection means.

7. An X-ray tube according to claim 1 wherein the said correction means is arranged to incline the said beam of electrons, to the undeflected beam, through an angle dependent on the said deflection to maintain the region of incidence of the deflected beam substantially parallel to that of the undeflected beam despite the inclined disposition of the surface of said target.

8. An X-ray tube according to claim 7 wherein the correction means is arranged to incline the said beam of electrons through an angle $\beta$ to the undeflected beam such that $\beta$ is given as $\tan^{-1}(\tan\theta \tan\alpha)$ where $\theta$ is the deflection angle and $\alpha$ is the angle by which the surface of the target is inclined to the second direction.

9. An X-ray tube according to claim 7 including four coils, two being disposed on each side of the said beam in the first direction, arranged so that adjacent coils produce magnetic fields of opposite polarity.

10. An X-ray tube according to claim 7 wherein said correction means includes a coil system arranged to incline said beam to the undeflected beam and to introduce a precurvature of said beam to maintain the region of incidence of the undeflected beam substantially parallel to the region of incidence of the undeflected beam.

11. An X-ray tube according to claim 7 wherein the correction means comprises a coil system also arranged to form said deflection means.

12. A medical radiographic apparatus including: an X-ray tube having a source of a ribbon-like beam of electrons and a target electrode extending in a first direction substantially perpendicular to the direction of travel of the undeflected electrons and having a surface inclined to the said direction of travel of the undeflected electrons to direct X-rays, produced by impact of the electrons on the target, through a patient position; detector means arranged to provide output signals indicative of the intensity of the radiation after passage through the patient position; means for scanning the electrons along the target in the said first direction to direct X-ray through the patient position along different paths; means for chaning the form of the beam of electrons in proportion to the said deflection so that the region of incidence of the deflected beam on the target remains substantially parallel to the region of incidence of the undeflected beam; and processing means arranged to process the said output signals to provide a distribution of the absorption of the radiation in a region of a body inserted in the patient position.

* * * * *

UNITED STATES PATENT AND TRADEMARK OFFICE
CERTIFICATE OF CORRECTION

PATENT NO. : 4,039,807
DATED : August 2, 1977
INVENTOR(S) : ERIC WILLIAM BULL

It is certified that error appears in the above-identified patent and that said Letters Patent are hereby corrected as shown below:

Column 4, line 4, delete "5°" and insert -- 50° --.

Column 4, line 54, delete "for that" and insert -- that for --.

Column 8, line 26, (Claim 12), after "direct" and before "X-ray" insert -- the --.

Column 8, line 27, (Claim 12), delete "chaning" and insert -- changing --.

Signed and Sealed this

Fifteenth Day of May 1979

[SEAL]

Attest:

RUTH C. MASON
Attesting Officer

DONALD W. BANNER
Commissioner of Patents and Trademarks